(12) United States Patent
Posca

(10) Patent No.: US 10,045,841 B2
(45) Date of Patent: Aug. 14, 2018

(54) APPARATUS FOR MAKING DENTAL PROSTHESES AND RELATED METHODS

(71) Applicant: TCS, INC., Signal Hill, CA (US)

(72) Inventor: Jorge Posca, Long Beach, CA (US)

(73) Assignee: TCS, Inc, Signal Hill, CA (US)

( * ) Notice: Subject to any disclaimer, the term of this patent is extended or adjusted under 35 U.S.C. 154(b) by 189 days.

(21) Appl. No.: 15/049,478

(22) Filed: Feb. 22, 2016

(65) Prior Publication Data

US 2016/0250007 A1  Sep. 1, 2016

Related U.S. Application Data

(60) Provisional application No. 62/121,964, filed on Feb. 27, 2015.

(51) Int. Cl.
*A61C 13/08* (2006.01)
*A61C 13/20* (2006.01)
*B65D 83/20* (2006.01)
*A61C 13/12* (2006.01)

(52) U.S. Cl.
CPC .......... *A61C 13/081* (2013.01); *A61C 13/206* (2013.01); *B65D 83/206* (2013.01); *A61C 13/12* (2013.01)

(58) Field of Classification Search
CPC ...... A61C 13/081; A61C 13/12; A61C 13/206
See application file for complete search history.

(56) References Cited

U.S. PATENT DOCUMENTS 7,303,392 B1   12/2007   Schermerhorn et al.

*Primary Examiner* — James Sanders
(74) *Attorney, Agent, or Firm* — Roland J. Tong

(57) ABSTRACT

Apparatus and methods for making dental prostheses including a matrix housing that has a plurality of interconnected walls, one of which defines an aperture. The matrix housing houses a dental model of a set of teeth, a wax model of a clasp, and a matrix that defines a sprue. The aperture provides access to the sprue. The matrix housing may be used with a cartridge for containing thermoplastic resin and a resin discharging device. The discharging device includes a body defining a through hole, a cartridge mount attached to the body, a ratchet push rod inserted through the through hole and including a plurality of teeth, a trigger pivotably attached to the body, and a drive tooth connected to the trigger and the body. The drive tooth cooperates with the teeth of the push rod to control the pressure asserted by the push rod to the cartridge.

10 Claims, 9 Drawing Sheets

APPARATUS FOR MAKING DENTAL PROSTHESES AND RELATED METHODS

CROSS-REFERENCE TO RELATED APPLICATIONS

This application claims the benefit of U.S. Provisional Application No. 62/121,964 filed Feb. 27, 2015, the disclosure of which is incorporated in its entirety by reference herein.

TECHNICAL FIELD

The present disclosure relates to apparatus and methods in dentistry, particularly those relating to making dental prostheses.

BACKGROUND

A removable partial denture is a dental prosthetic consisting of one or more artificial teeth that can be removed from the mouth. The process of making a removable partial denture starts at a dental office, where a dentist takes an impression of a patient's teeth and gums as well as the patient's bite registration. The patient's bite registration is a recording of how the patient's upper and lower teeth fit together when the patient bites down. A dental mould typically made of plaster is created based on the impression and bite registration. A wax model of a clasp or partial that has artificial gums and at least one tooth is created from the dental mould. The wax model is surrounded with matrix material and then subjected to boiling water, which melts away the wax and separates the negative of the clasp or partial from the wax. A thermoplastic resin is added to the matrix material and then placed in bulky, large-scale and expensive hot press equipment. The hot press equipment can be very costly and may not be available in many places desiring to make dental prostheses.

SUMMARY

One aspect of the present disclosure relates to an apparatus for making dental prostheses including a matrix housing that has a plurality of interconnected walls. One of the walls defines an aperture. The matrix housing holds a dental model of a set of teeth, a wax model of a clasp, and a matrix that defines a sprue. The aperture provides access to the sprue. In certain embodiments, one of the walls is moveable to allow the dental model, the wax model of a clasp, and the matrix to be placed inside the matrix housing. The interconnected walls include a base and a pair of opposing sidewalls perpendicularly attached to the base. One of the sidewalls defines a sprue access hole, which leads to a sprue of a matrix. In another embodiment, one of the walls is a detachable wall. The detachable wall defines an aperture, which provides access to the sprue. The detachable wall includes a retaining wall perpendicularly attached to it. The interconnected walls include a base, a first wall perpendicular to the base, and a second wall parallel to the first wall. The first and second walls define a slot adapted to receive the retaining wall. The second wall serves as an outer wall of the housing and defines a recess adapted to receive a fastener. The fastener secures the detachable wall to the housing, which is preferably made of thermally conductive material.

Another aspect of the present disclosure relates to a process of making a dental prosthesis. The process includes the steps of providing a matrix housing including a plurality of interconnected walls with one of the walls defining an aperture, positioning a wax model of a clasp inside the matrix housing, surrounding the wax model with a matrix, forming a sprue within the matrix, aligning the sprue with the aperture of the matrix housing, heating the matrix housing and the wax model positioned inside the matrix housing, and injecting a thermoplastic resin through the aperture of the matrix housing and into the sprue. In certain embodiments, the process includes placing a thermoplastic resin in a thermally conductive cartridge, providing a heater that is detached from the thermally conductive cartridge, and heating the thermally conductive cartridge in the heater.

The process may further include the steps of placing a thermoplastic resin in a thermally conductive cartridge and holding the thermally conductive cartridge with a resin discharging device. The resin discharging device includes: a body defining a through hole; a cartridge mount that is attached to the body and that holds the cartridge; a ratchet push rod inserted through the through hole and including a plurality of teeth; a trigger pivotably attached to the body; and a drive tooth attached to the trigger and the body, the drive tooth adapted to cooperate with the teeth of the push rod to control distance travelled by the ratchet push rod within the body and pressure asserted by the push rod to the cartridge.

Another aspect of the present disclosure relates to an apparatus for making dental prostheses comprising: a cartridge for containing thermoplastic resin; a resin discharging device that includes a body defining a through hole; a cartridge mount attached to the body and adapted to hold the cartridge; a ratchet push rod inserted through the through hole and including a plurality of teeth; a trigger pivotably attached to the body; and, a drive tooth attached to the trigger and the body. The drive tooth cooperates with the teeth of the push rod to control distance travelled by the ratchet push rod within the body and pressure asserted by the push rod to the cartridge.

DETAILED DESCRIPTION

As required, detailed embodiments of the present invention are disclosed herein; however, it is to be understood that the disclosed embodiments are merely exemplary of the invention that may be embodied in various and alternative forms. The figures are not necessarily to scale; some features may be exaggerated or minimized to show details of particular components. Therefore, specific structural and functional details disclosed herein are not to be interpreted as limiting, but merely as a representative basis for teaching one skilled in the art to variously employ the present invention.

Figure 1:
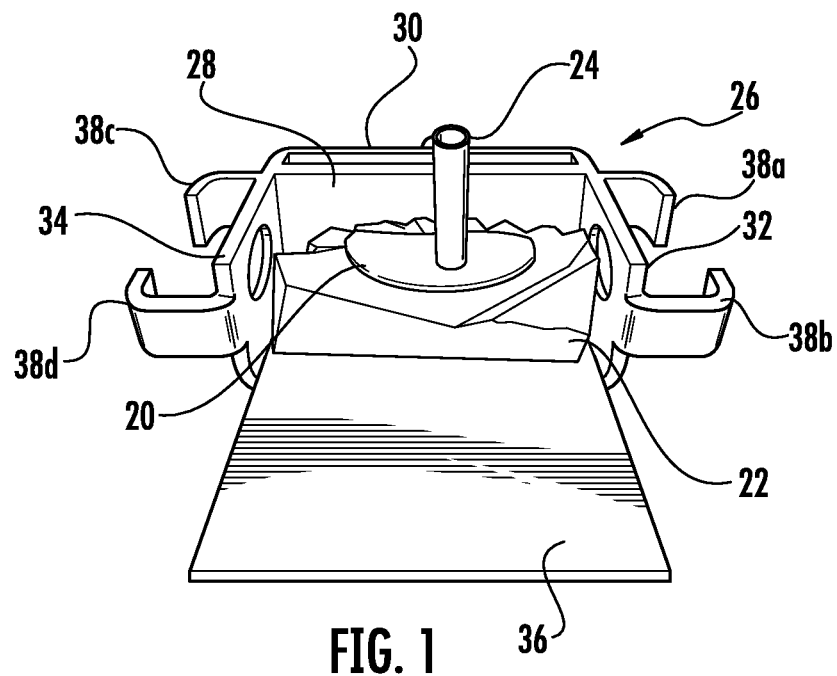
FIG. 1 is a front view of a dental model with wax and a sprue mold placed on a housing of the present disclosure.

The present disclosure relates to apparatus and methods for making dental prostheses. Referring to FIG. 1, wax 20 is placed over a dental model or impression 22 of teeth and gums. The dental model 22 may be a partial dental model, and the wax 20 may be placed over the dental model 22 to make a wax model of a dental clasp or partial denture. A sprue mold 24 is placed approximately in the center of the wax. The sprue mold 24 may be a tubular metal that is used to form a sprue or passage for a thermoplastic resin to reach the wax 20 that will be surrounded by a matrix material, as will be discussed below. The dental model 22, the wax 20 that is on the dental model 22, and the sprue mold 24 that is attached to the wax 20 are positioned inside a housing 26. The housing 26 is formed by several interconnected walls, including a first back wall 28, a second back wall 30 that is parallel with the first back wall 28, a right side wall 32 perpendicularly attached to the back walls, and a left side wall 34 also perpendicularly attached to the back walls and opposite to the right side wall 32. The walls are attached to a base wall 36, which supports the walls and maintains the upright position of the walls. The base wall 36 provides a surface to where the dental model 22 with the wax 20 and the sprue mold 24 is laid. Several handles 38a-d may be attached to the side walls of the housing 26 so the housing can easily be grabbed during the casting process.

Figure 2:
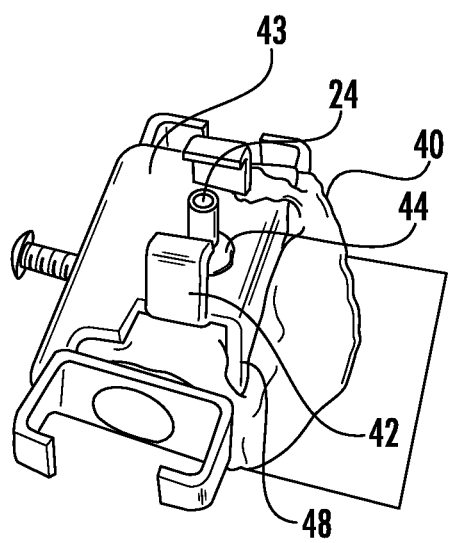
FIG. 2 is a top view of a cover placed on top of the housing that contains the dental model with wax covered by matrix material.
Figure 3:
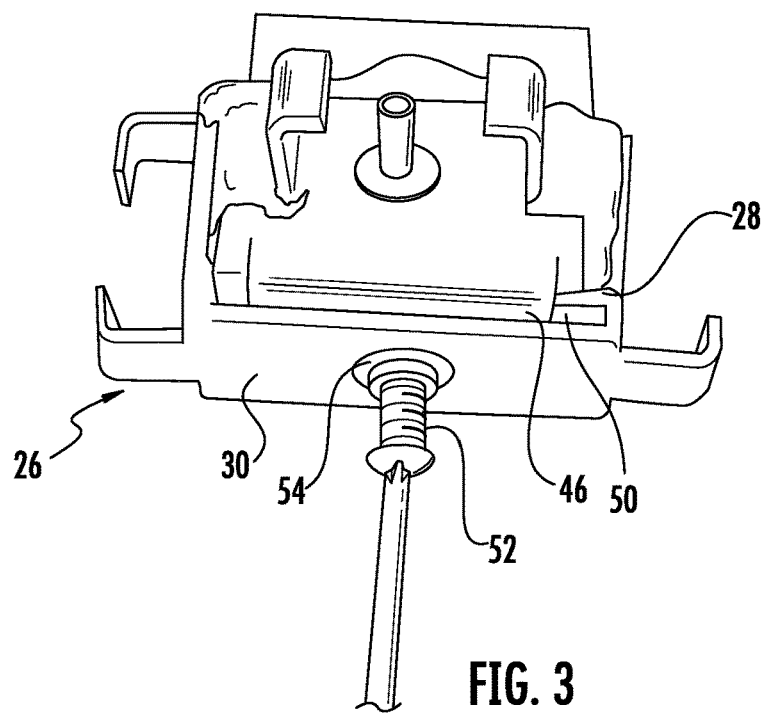
FIG. 3 is a top view of the cover being fastened to the housing.

Referring to FIG. 2, the dental model 22 with the wax 20 and the sprue mold 24 is surrounded by a matrix material 40. The matrix material 40 may be a silicone impression putty, which is known in the art, or a plaster material. The housing 26 includes a removable cover 42 that has a top wall 43 and a pair of opposing tabs 46 and 48 extending perpendicularly downwards from the top wall 43. The removable cover 42 defines an aperture 44 that can receive the sprue mold 24. The removable cover 42 is placed on top of the housing 26 to close the housing 26 and encase the dental model 22 with the wax 20, the sprue mold 24, and the matrix material 40. The sprue mold 24 is inserted into the aperture 44. Excess matrix material 40 outside the confines of the walls of the housing 26 is removed. Referring to FIG. 3, tab 46 of the cover 42 is inserted into a slot 50 that is formed as a gap between the first back wall 28 and the second back wall 30 to close the housing 26. A fastener 52 is used to fasten the cover 42 to the housing 26. The second back wall 30 defines a recess 54 that receives the fastener 52, which fastens the cover 42 against the first back wall 28.

Figure 4:
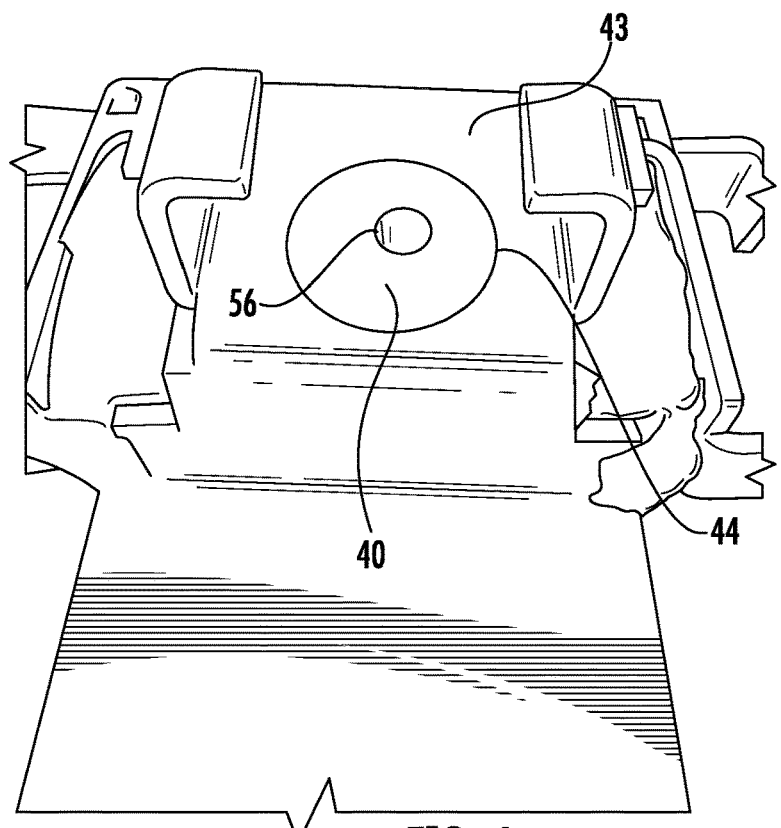
FIG. 4 is a front view of the sprue mold removed from the matrix material inside the housing to form a sprue.
Figure 5:
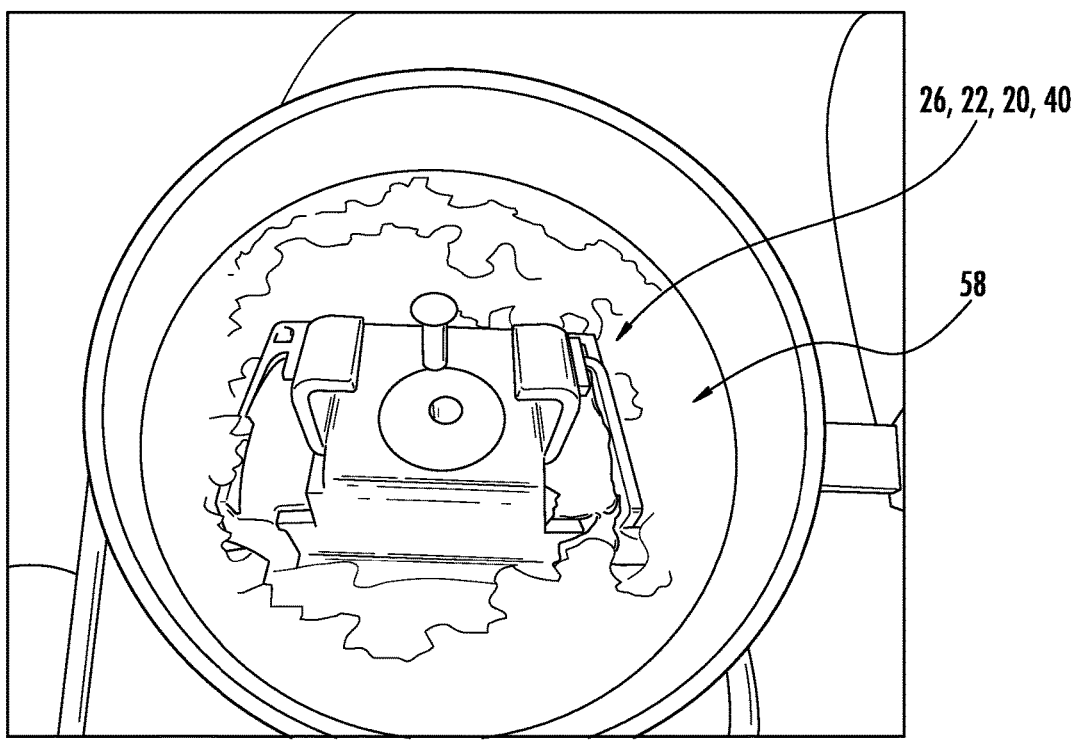
FIG. 5 is a top view of the housing containing a dental model with wax covered by matrix material being heated in a boiling water to melt the wax.

Next, in FIG. 4, the sprue mold 24 is removed from the dental model 22. The sprue mold 24 leaves a sprue 56 that leads to the wax 20. The aperture 44 defined by the top wall 43 of the cover 42 creates a continuous hole with the sprue 56. The housing 26 that encases the dental model 22 with the wax 20 and the matrix material 40 is placed in a boiling water for an amount of time sufficient to melt the wax 20 (FIG. 5).

Figure 6:
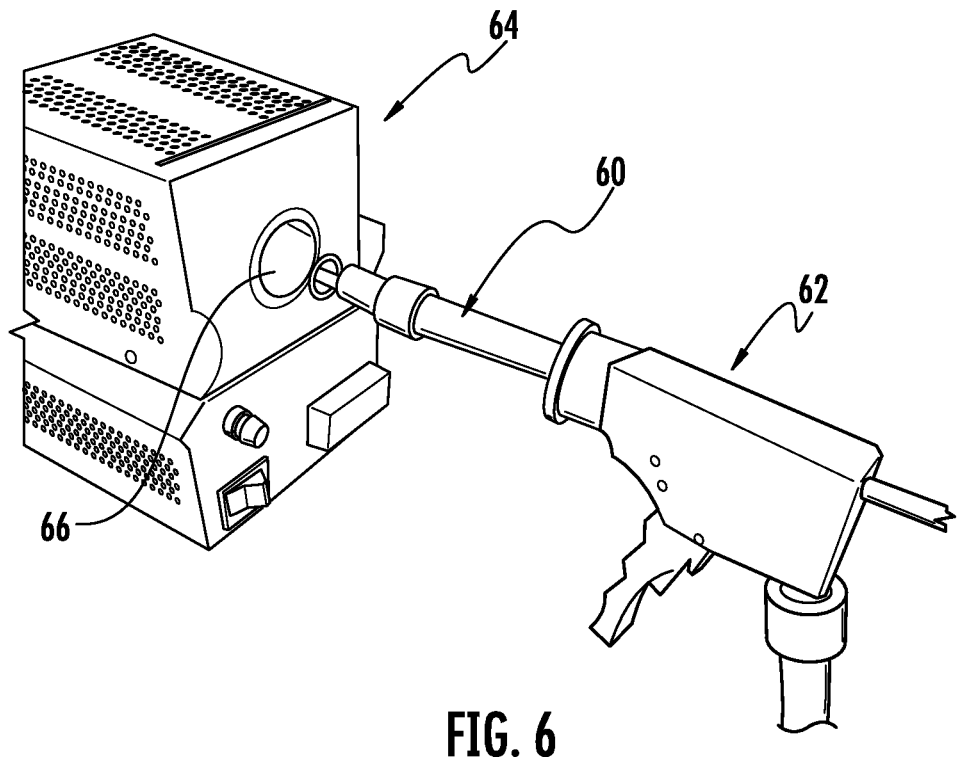
FIG. 6 is a perspective view of a cartridge containing a thermoplastic resin and a discharging device holding the cartridge.
Figure 7:
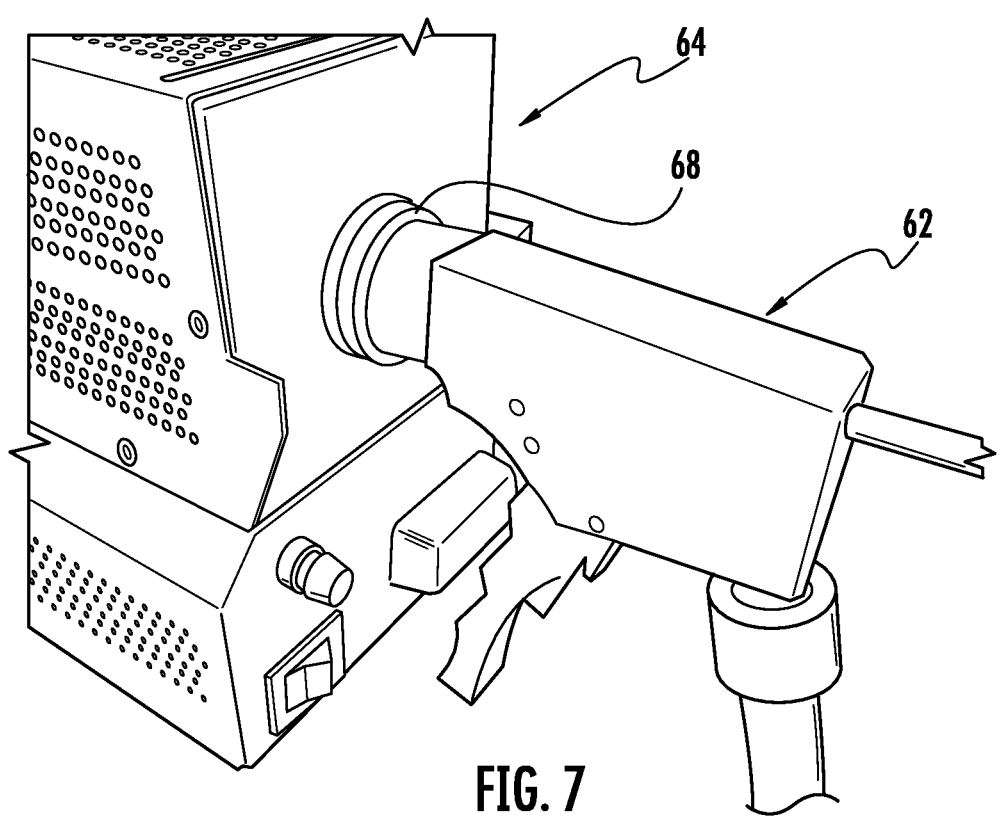
FIG. 7 is a perspective view of the cartridge being held by a discharging device and inserted into a heater.
Figure 8:
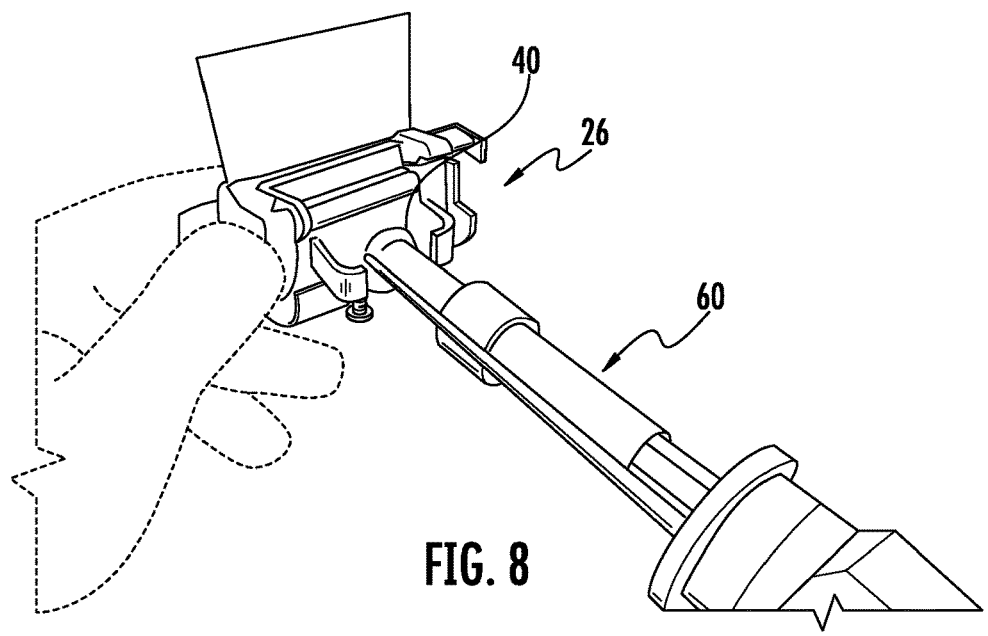
FIG. 8 is a perspective view of the cartridge being inserted into the sprue and the discharging device being used to inject resin into the sprue.
Figure 9:
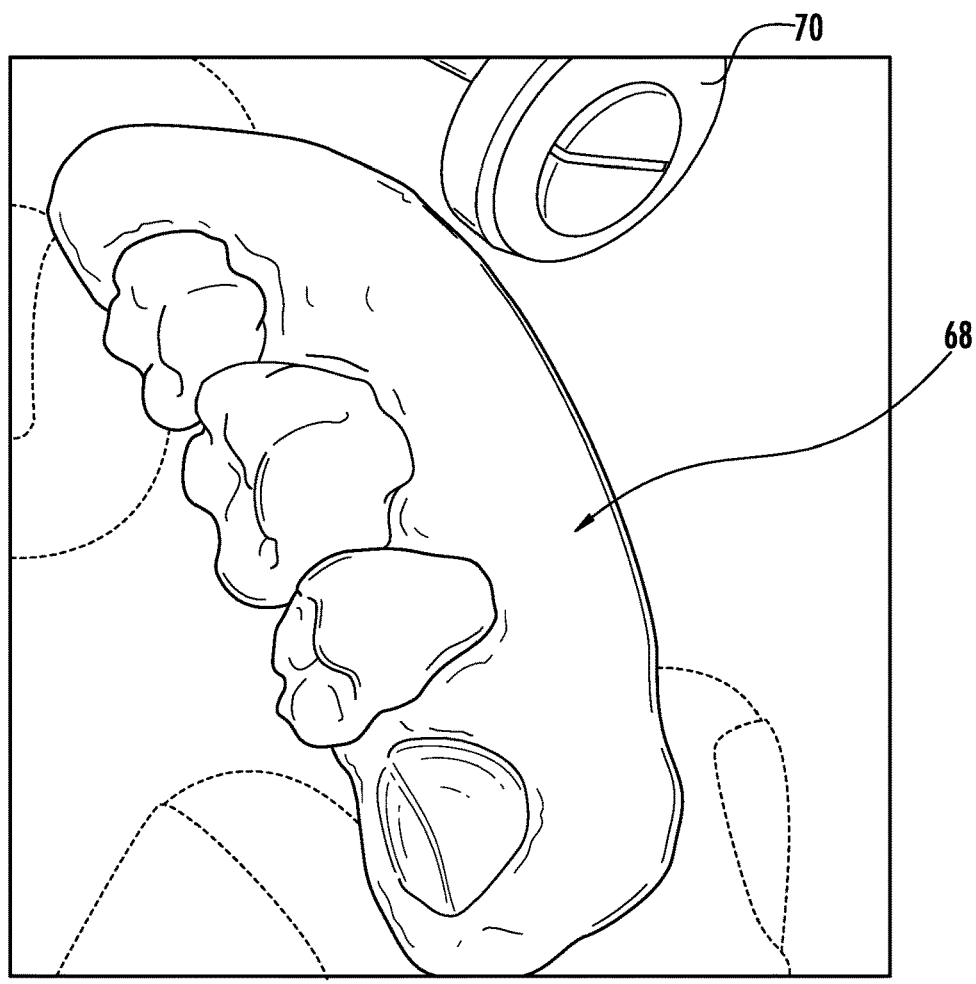
FIG. 9 is a top view of the dental prosthesis that is made from the steps shown in FIGS. 1-8 being polished.

Referring to FIG. 6, a resin cartridge 60 mounted on a discharging device 62 is shown. The resin cartridge 60 contains thermoplastic resin, which is known in the art. An external heater 64 is provided and defines a cartridge receiver opening 66. The thermoplastic resin is heated by the external heater 64 by inserting the resin cartridge 60 into the cartridge receiver opening 66 of the external heater 64 (FIG. 7). The discharging device 62 includes a heat proof disk 68 that encloses the cartridge 60 within the confines of the external heater 64. The amount of heating time depends on the thermoplastic resin used. Ideally, the thermoplastic resin is heated until it becomes liquefied enough to come out of the cartridge when pressure is inserted by the discharging device. Referring to FIG. 8, the cartridge 60 is inserted into the sprue 56 (from FIG. 4) so the thermoplastic resin can be injected into the matrix material 40 that is contained in the housing 26. The discharging device 62 applies pressure to a soft compressible back wall of the cartridge to squeeze the resin out of the cartridge. The soft compressible back wall of the cartridge may be a rubber septum. The resin is allowed to cool within the matrix, which may be about two minutes. Optionally, the housing 26 containing the dental model 40, the wax 20, the resin, and the matrix material 40 can be placed in a cold water bath to allow the resin to harden. Once the resin has hardened, the housing 26 may be opened by removing the cover 42. The wax 20 may be separated from the dental model 20 and the matrix material 40. A partial denture or clasp 68 is formed from the process described above. The clasp 68 can then be polished using a polishing device 70 (FIG. 9).

Figure 10:
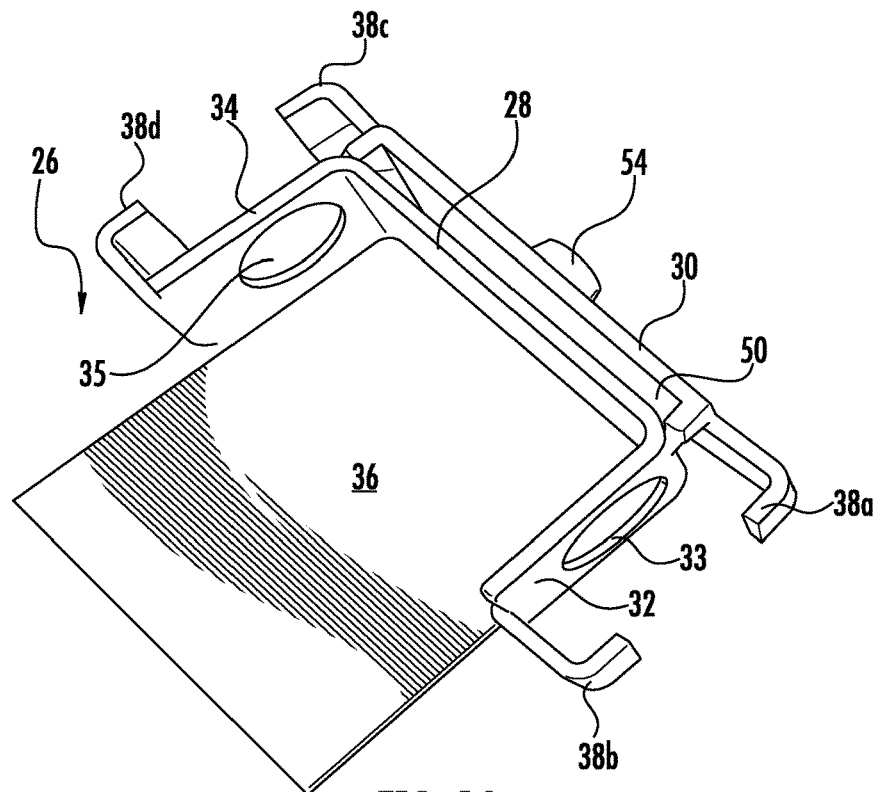
FIG. 10 is a perspective view of a housing portion including a base, opposing sidewalls perpendicularly attached to the base, and back walls perpendicularly attached to the sidewalls.

The present disclosure includes several casting apparatus. Referring to FIG. 10, the apparatus includes a matrix housing 26 that is formed by interconnected walls. The matrix housing 26 is formed by a base wall 36, a first back wall 28 perpendicularly attached to and extending upright from the base wall 36, and a pair of opposing side walls—right side wall 32 and left side wall 34. The right side wall 32 defines a sprue aperture 33, and the left side wall 34 also defines a sprue aperture 35. The sprue apertures 33 and 35 can be aligned with sprues that are formed from a matrix material to allow thermoplastic resin to be injected through them and to reach the wax. Housing handles 38b and 38d are attached to the right side wall 32 and the left side wall 34, respectively. The housing handles 38b and 38d may be L-shaped handles.

Figure 11:
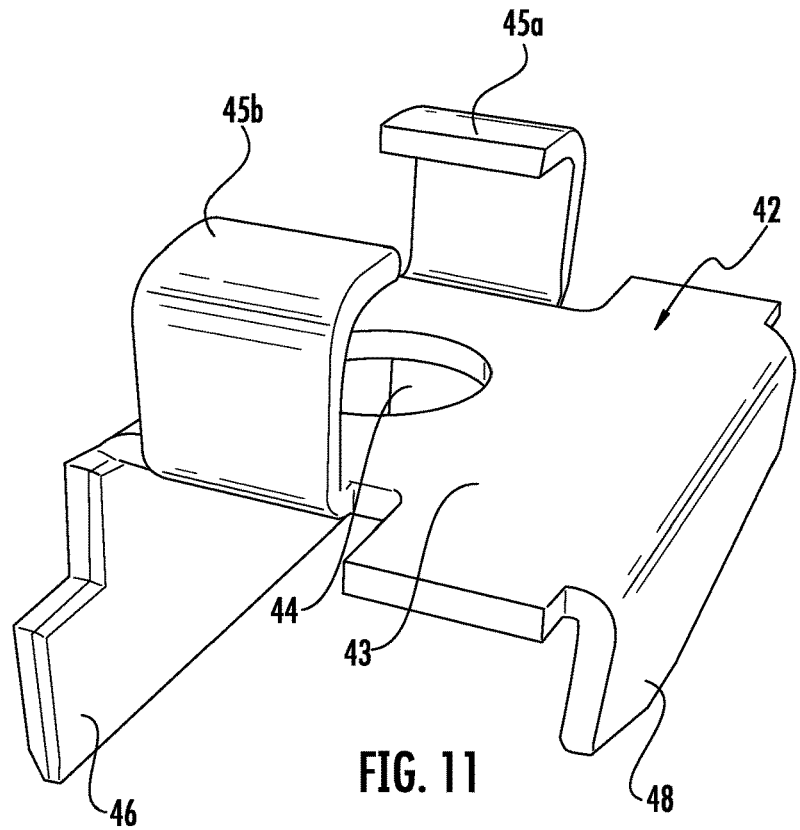
FIG. 11 is a perspective view of a housing cover.

A second back wall 30 is also attached to and extending upright from the base wall 36. The second back wall 30 is parallel to the first back wall 28. Housing handles 38a and 38b are attached to the both sides of the second wall 30 and may also be L-shaped. A slot 50 is formed in between the first back wall 28 and the second back wall 30 to receive tab 46 or retaining wall of the cover 42. Referring to FIG. 11, cover 42 includes a top wall 43 that provides a top surface. The top wall 43 defines an aperture 44, which can be aligned with a sprue formed from a matrix material to allow thermoplastic resin to be injected through them to reach the wax. A pair of tabs extends perpendicularly downwards from the top wall 43—tabs 46 and 48. A pair of handles 45a and 45b also extends perpendicularly upwards from the top wall 43. The handles 45a and 45b may be L-shaped.

Figure 12:
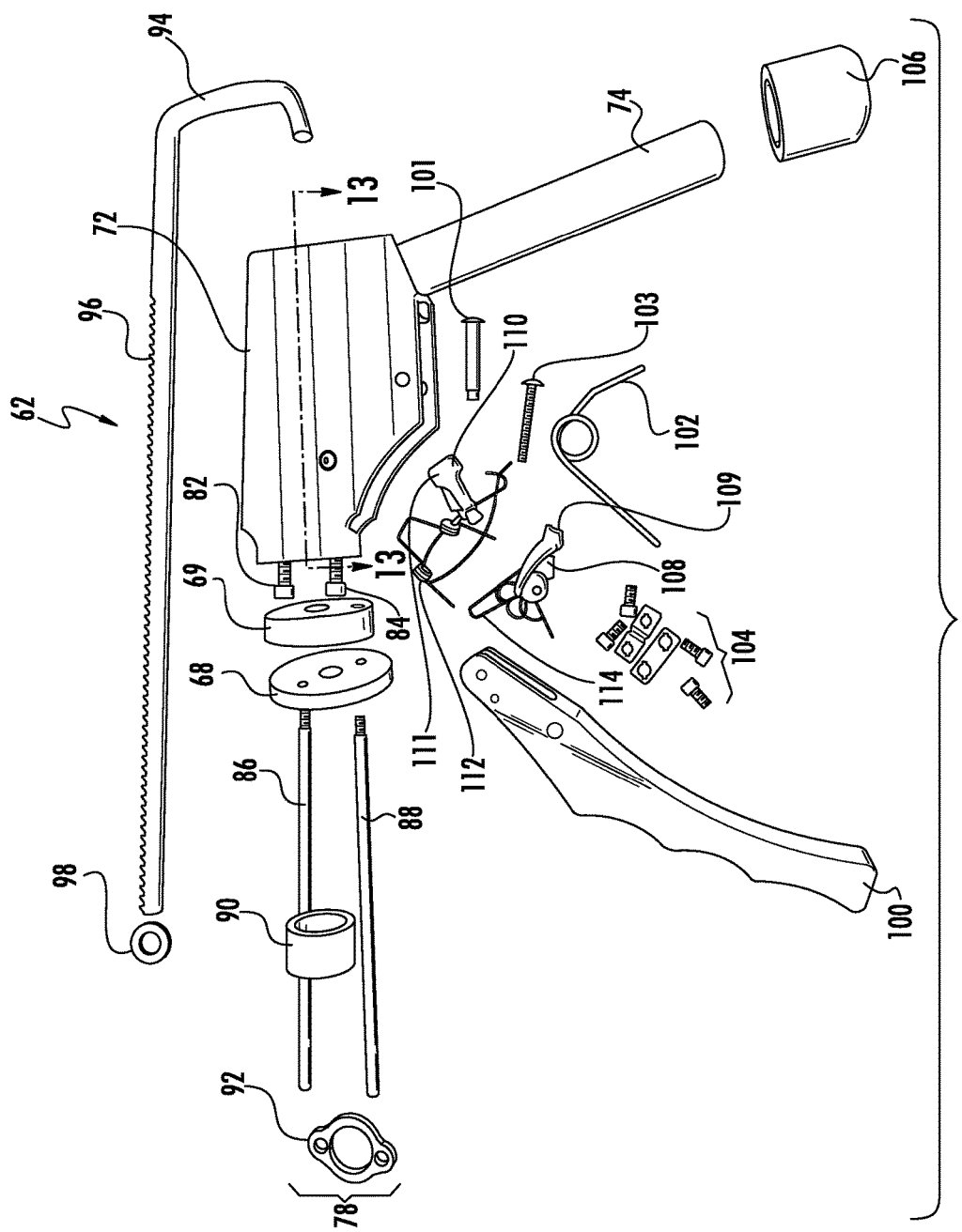
FIG. 12 is an exploded view of a discharging device for discharging thermoplastic resin.

Referring to FIG. 12, another casting apparatus in the form of a discharge device 62 is shown. Discharge device 62 includes a body 72, a handle 74 attached below the body 72, and a trigger 100 pivotably attached below the body 72. A cartridge mount assembly 78 is attached to the body 72 and serves to hold a cartridge containing thermoplastic resin. The cartridge mount assembly 78 includes a pair of parallel arms 86 and 88 that attaches to the body 72 via a pair of fasteners 82 and 84. A pair of disks 69 and 68 is in between the arms and the fasteners. The disks 69 and 68 serve to control and stop the discharge device 62 from going further into the external heater when heating the cartridge. A first cartridge control ring 90 lies along the arms 86 and 88 to give the cartridge a snug fit. A second cartridge control ring 92 is attached at the end of the arms 86 and 88 to hold the cartridge.

The body 72 defines a through hole that runs horizontally across the body 72 and that receives a ratchet push rod 94. The ratchet push rod 94 is inserted from one end of the body 72, through the disks 68 and 69, and in between the arms 86 and 88. The ratchet push rod 94 contacts the cartridge and applies pressure on the soft compressible back wall of the cartridge to discharge the thermoplastic resin contained in the cartridge. A trigger 100 is pivotably attached to the body 72 via a pivot bolt 101 and controls the movement of the ratchet push rod 94. A biasing device 102 has one leg that attaches to the trigger via spring fasteners 104 and another leg that attaches to the handle 74 via a spring holder 106. Inside the trigger 100 are springs 114 and a pawl 108. The body 72 also has its springs 112 and pawl 110 that are attached inside the body 72 via a fastener 103. Each pawl 108 and 110 has its own respective drive tooth 109 and 111. Springs 114 and pawl 108 of the trigger 100 work with the springs 112 and pawl 110 of the body 72 so that pawl 110 can engage and disengage with one of the teeth 96 of the ratchet push rod 94 to control the movement of the ratchet push rod 94.

Figure 13:
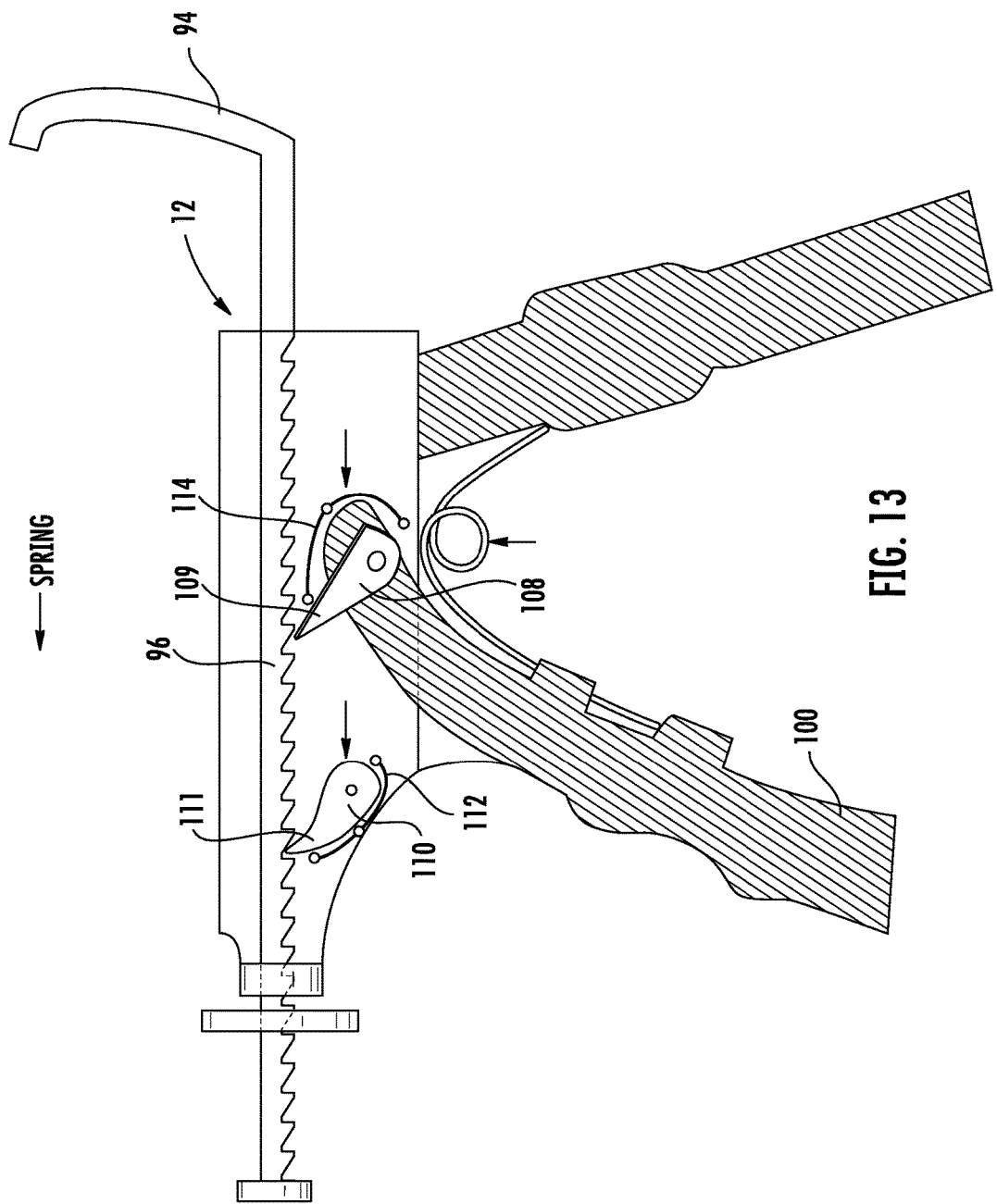
FIG. 13 is a cross-section view of the body, the trigger, and the handle of the discharging device taken from lines 13-13 as shown in FIG. 12.

Referring to FIG. 13, pawl 110 is positioned inside the body 72 and is moveably connected to a spring 112. Pawl 110 has a drive tooth 111 that moves to engage and disengage with one of the teeth 96 of the ratchet push rod 94. Another pawl, pawl 108, is positioned inside the body 72 and the handle 100. Spring 114 moveably connects pawl 108 to the trigger 100 and the body 72. Spring 112 and spring 114 are connected to each other so that when the trigger 100 is pressed, drive tooth 111 of pawl 110 and drive tooth 109 of the pawl 108 simultaneously disengage from one of the teeth 96 of the ratchet push rod 94. When the trigger 100 is released, drive tooth 111 of pawl 110 and drive tooth 109 of the pawl 108 simultaneously engage with one of the teeth 96 of the ratchet push rod 94. To add pressure on the cartridge, the push rod 94 may be moved in the arrow shown when the trigger 100 is pressed and the drive teeth 109 and 111 are disengaged from the teeth 96 of the ratchet push rod 94.

Figure 14:
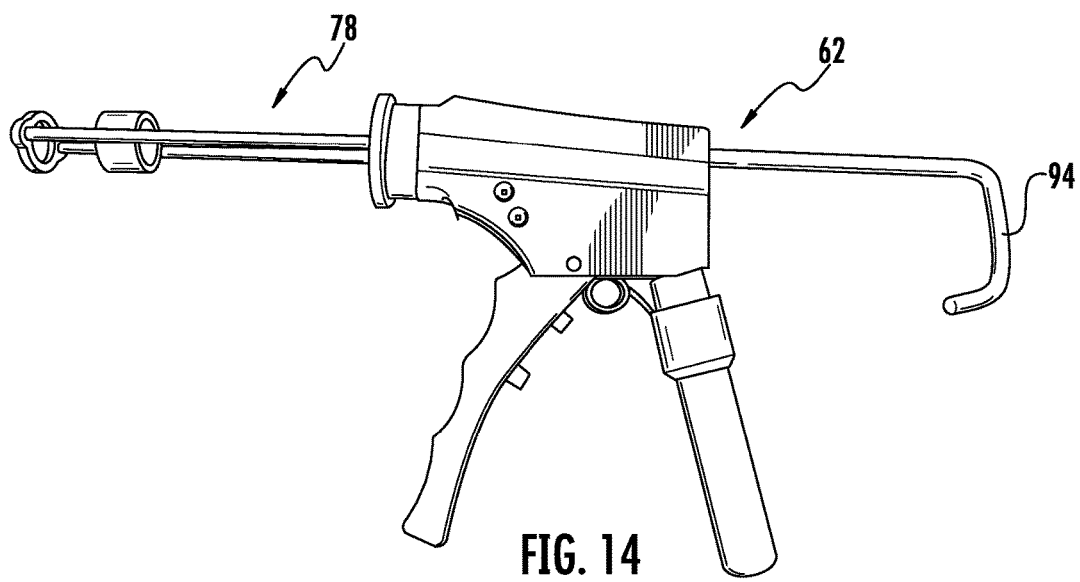
FIG. 14 is a front view of the discharging device without the cartridge.
Figure 15:
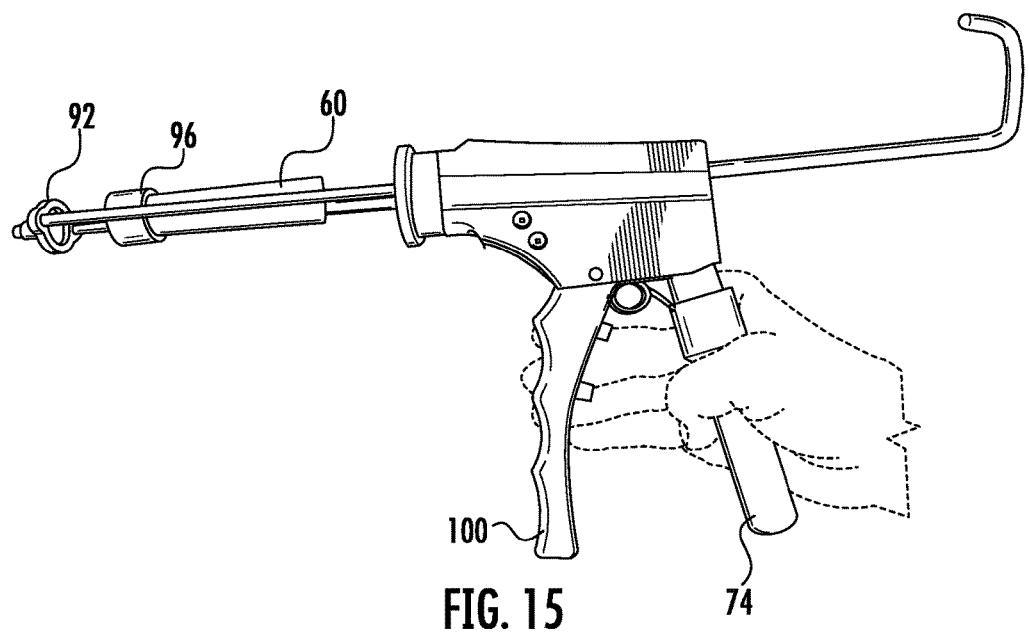
FIG. 15 is a front view of the discharging device with the cartridge attached to the cartridge mount.

Referring to FIG. 14, the discharge device 62 is shown without a cartridge and with the ratchet push rod 94 in a deactivated position that is away from the cartridge mount assembly 78. In FIG. 15, a cartridge 60 has its body inserted through and held by the first cartridge control ring 90. The cartridge 60 has its tip surrounded and supported by the second cartridge control ring 92. The trigger 100 is pressed towards the handle 74, which in turn, moves the ratchet push rod 94 to its activated position. In the activated position, the ratchet push rod 94 contacts the cartridge 60. A tooth of the ratchet push rod 94 is engaged with the pawl 108 that holds the position of the ratchet push rod 94. As the ratchet push rod 94 contacts and applies pressure to the cartridge 60, thermoplastic resin is discharged from the cartridge 60.

While exemplary embodiments are described above, it is not intended that these embodiments describe all possible forms of the invention. Rather, the words used in the specification are words of description rather than limitation, and it is understood that various changes may be made without departing from the spirit and scope of the invention. Additionally, the features of various implementing embodiments may be combined to form further embodiments of the invention.

What is claimed is:

1. An apparatus for making dental prostheses comprising:
a matrix housing including a plurality of interconnected walls, one of the walls defining an aperture, the matrix housing adapted to hold a dental model of a set of teeth, a wax model of a clasp, and a matrix that defines a sprue, wherein the aperture provides access to the sprue;
wherein one of the walls is a detachable wall adapted to be detachable from the plurality of interconnected walls, the detachable wall defining an aperture, the matrix housing adapted to hold a dental model of a set of teeth, a wax model of a clasp, and a matrix that defines a sprue, wherein the aperture provides access to the sprue; and
wherein the detachable wall includes a retaining wall perpendicularly attached to the detachable wall, the plurality of interconnected walls includes a base, a first wall perpendicular to the base, a second wall parallel to the first wall, the first and second wall defining a slot adapted to receive the retaining wall.

2. The apparatus of claim 1, wherein one of the walls is moveable to allow the dental model, the wax model of a clasp, and the matrix to be placed inside the matrix housing.

3. The apparatus of claim 1, wherein the plurality of interconnected walls includes a base and a pair of opposing sidewalls perpendicularly attached to the base, at least one of the sidewalls defining a sprue access hole, the sprue access hole adapted to lead to a sprue of a matrix positioned in the matrix housing.

4. The apparatus of claim 1, wherein the second wall serves as an outer wall of the housing, the second wall defining a recess adapted to receive a fastener, the fastener being adapted to secure the detachable wall to the housing.

5. The apparatus of claim 1, wherein the housing is thermally conductive.

6. An apparatus for making dental prostheses comprising:
a cartridge for containing thermoplastic resin;
a resin discharging device that includes:
a body defining a through hole;
a cartridge mount attached to the body and adapted to hold the cartridge;
a ratchet push rod inserted through the through hole and including a plurality of teeth;
a trigger pivotably attached to the body;
a drive tooth attached to the trigger and the body, the drive tooth adapted to cooperate with the teeth of the push rod to control distance travelled by the ratchet push rod within the body and pressure asserted by the push rod to the cartridge; and
a matrix housing including a plurality of interconnected walls, at least one of the walls defining an aperture, the matrix housing adapted to hold a dental model of a set of teeth, a wax model of a clasp, and a matrix that defines a sprue, wherein the aperture provides access to the sprue and the thermoplastic resin can be injected into the sprue by holding the cartridge with the resin discharging device, inserting the cartridge into the aperture, and applying pressure on the trigger to apply pressure on the cartridge and to discharge the thermoplastic resin into the sprue;

wherein one of the walls is a detachable wall adapted to be detachable from the plurality of interconnected walls, the detachable wall defining an aperture, the matrix housing adapted to hold a dental model of a set of teeth, a wax model of a clasp, and a matrix that defines a sprue, wherein the aperture provides access to the sprue; and wherein the detachable wall includes a retaining wall perpendicularly attached to the detachable wall, the plurality of interconnected walls includes a base, a first wall perpendicular to the base, a second wall parallel to the first wall, the first and second wall defining a slot adapted to receive the retaining wall.

7. The apparatus of claim 6, wherein one of the walls is moveable to allow the dental model, the wax model of a clasp, and the matrix to be placed inside the matrix housing.

8. The apparatus of claim 6, wherein the plurality of interconnected walls includes a base and a pair of opposing sidewalls perpendicularly attached to the base, one of the sidewalls defining a sprue access hole, the sprue access hole adapted to lead to a sprue of a matrix positioned in the matrix housing.

9. The apparatus of claim 6, wherein the second wall serves as an outer wall of the housing, the second wall defining a recess adapted to receive a fastener, the fastener being adapted to secure the detachable wall to the housing.

10. The apparatus of claim 6, further comprising an external heater separate from the resin discharging device, the external heater defining a receiving aperture for the cartridge, wherein when the cartridge is inserted into the receiving aperture, the external heater heats the cartridge.

* * * * *